United States Patent
Kooiman

[11] Patent Number: 5,915,961
[45] Date of Patent: *Jun. 29, 1999

[54] TENSIONING SYSTEM FOR AN ORTHODONTIC OUTER BRACE

[76] Inventor: Johan Anton Kooiman, Bodegraafsestraat 26, NL-2805 GR Gouda, Netherlands

[*] Notice: This patent is subject to a terminal disclaimer.

[21] Appl. No.: 08/884,653

[22] Filed: Jun. 27, 1997

Related U.S. Application Data

[62] Division of application No. 08/464,895, Jun. 29, 1995, Pat. No. 5,667,380.

[30] Foreign Application Priority Data

Jan. 5, 1994 [NL] Netherlands ............................ 9400009

[51] Int. Cl.⁶ .................................................... A61C 3/00
[52] U.S. Cl. .......................................................... 433/5
[58] Field of Search ...................................... 433/5

[56] References Cited

U.S. PATENT DOCUMENTS

| | | | |
|---|---|---|---|
| 3,526,035 | 9/1970 | Armstrong | 433/5 |
| 3,918,159 | 11/1975 | Andrews | 433/5 |
| 4,037,324 | 7/1977 | Andreasen | 433/20 |
| 4,115,921 | 9/1978 | Armstrong | 433/5 |
| 4,226,589 | 10/1980 | Klein | 433/5 |
| 4,264,302 | 4/1981 | Wolk et al. | 433/5 |
| 4,553,933 | 11/1985 | Armstrong et al. | 433/5 |
| 4,553,934 | 11/1985 | Armstrong et al. | 433/5 |
| 4,849,032 | 7/1989 | Kawaguchi | 148/11.5 |
| 4,872,836 | 10/1989 | Grove | 433/5 |
| 5,046,948 | 9/1991 | Miura | 433/21 |
| 5,064,370 | 11/1991 | Jones | 433/21 |
| 5,551,871 | 9/1996 | Basselink et al. | 433/5 |
| 5,620,320 | 4/1997 | Luse et al. | 433/5 |

FOREIGN PATENT DOCUMENTS 0 198 579  10/1986  European Pat. Off. .
34 17 256  11/1985  Germany .

*Primary Examiner*—John J. Wilson
*Attorney, Agent, or Firm*—Young & Thompson

[57] ABSTRACT

A tensioning system for an orthodontic outer brace includes a resilient element and coupler for transmitting a tensile force exerted by the resilient element to the outer brace. The tensioning system involves an arc-shaped guide path, along which the resilient element is freely movable. The resilient element preferably has a spring constant which decreases or is zero on further extension after a specific spring force or extension is reached. The resilient element is preferably a helical spring.

3 Claims, 4 Drawing Sheets

TENSIONING SYSTEM FOR AN ORTHODONTIC OUTER BRACE

This application is a division of application Ser. No. 08/464,895, filed Jun. 29, 1995, now U.S. Pat. No. 5,667,380.

DESCRIPTION

The present invention relates to a tensioning system for an orthodontic outer brace, comprising resilient means, and coupling means for transmitting a tensile force exerted by the resilient means to the outer brace.

Tensioning systems of this type are generally known, for example from U.S. Pat. No. 3,526,035. This patent discloses a tensioning system for a so-called neck brace, comprising a neck band on which a strip of flexible material is mounted. Two small protective tubes are fixed to said strip, there being a spring in each tube. The springs are fixed on one side to the carrying strip and on the other side to one end of coupling means, which can be fixed to the outer brace by their other end. By stretching the respective springs and then fixing the coupling means to the outer brace in such a way that the springs remain stretched, a tensile force directed towards the neck is exerted on the outer brace. Via an inner brace fixed to the outer brace at the mouth, said tensile force is transmitted to two or more teeth, by which means the position of the latter can be corrected.

A further orthodontic outer brace having a tensioning system is disclosed in DE-A 3 417 256. In this case the neck band is slidably mounted in plastic guide sleeves. Said neck band is provided at both ends with perforations for adjustably fixing ends of resilient elements (in the form of elastic strips), which can be fixed at the opposite end to the outer brace itself. Resilient elements of this type attached to either side of the head between the ends of the neck band and the ends of the outer brace require a certain fitting length and fixing elements which seriously impede any freedom of head movement which the wearer may have. Moreover, accurate adjustment of a desired tensioning force for correction of the teeth is made more difficult by the interaction of the two resilient elements joined to one another by the neck band.

The comfort of tensioning systems of this type for the wearer leaves something to be desired because the freedom of movement of the head is impeded. If the patient turns his or her head to the left or the right (that is to say shakes his or her head to indicate no), an additional compressive force directed towards the left side or the right side of the teeth and backwards (that is to say towards the neck) will be exerted on the teeth concerned, whilst on the other side of the teeth a tensile force directed frontwards will be exerted on the teeth concerned which are located on the right or on the left. These additional forces can be fairly large, are unpleasant for the patient and are undesirable from the standpoint of the orthodontic treatment. Similar problems arise in the case of the movement of the head to indicate yes, in which case the resilient means are stretched further.

The aim of the present invention is to provide a tensioning system for an orthodontic outer brace with which the tensioning force to be transmitted to the teeth remains as constant as possible and the comfort for the wearer and the freedom of movement of the patient are increased.

According to the invention, this aim is achieved in that the resilient means comprise a resilient element, in that the tensioning system comprises an arc-shaped guide path, along which the resilient element is movable, and in that the coupling means can be fixed on one side to the outer brace and are connected to one another on the other side via the resilient element. As a result of these measures, the resilient element moves along the guide path when the patient turns his or her head. With this arrangement, the resilient element, such as, for example, an elastic band or a coil spring, is, as it were, fitted between two pairs of coupling means, such as, for example, two pieces of cord-like or strip-like material, in such a way that if a pull is exerted on one coupling means, a tensile force is transmitted via the spring to the other coupling means. The spring and the coupling means are able to move freely along the guide path in the direction of the guide path. If the tensioning system is fitted to a patient's neck and the coupling means are fixed to the outer brace, the entire unit, comprising the arms of the outer brace, the coupling means and the resilient element, forms, as it were, a closed "ring", which runs around the neck, the cheeks and the mouth of the patient. If the head is moved to the left or to the right, the "ring" turns in concert via the mouth and the outer brace, and the resilient element guided along the guide path will therefore move around in the same direction. With this arrangement, the resilient element will be subjected to no or hardly any additional stretching, as a result of which the forces exerted on the teeth remain virtually constant. Urge peaks in these compressive forces, such as occur with conventional tensioning systems, are largely avoided.

In order to protect the movable resilient element and to guarantee the free movability thereof, it is advantageous, according to the invention, for the guide path to comprise a tube. An additional advantage is that the patient's hair does not get caught in the resilient element and does not impede the movement backwards and forwards along the guide path.

To ensure optimum comfort in wear and to ensure that the resilient element is movable as flexibly as possible, it is advantageous, according to the invention, if the guide path is flexible, in such a way that the arc shape thereof can be adjusted to the curvature of the patient's neck. In this context, it is particularly advantageous if the arc shape, as it were, continually adjusts to the shape of the neck during use.

According to the invention, a flexible tubular guide path can be advantageously obtained by shaping the guide path from a wire or strip wound to give a spiral-like winding. However, ordinary tubes made of a flexible material are also very suitable.

In order to prevent, for example, the patient's hair from getting caught between the spiral-like winding it is advantageous, according to the invention, if the outside of the spiral-like winding, is provided with a covering which covers the winding.

Very supple movement of the resilient element is achieved, according to the invention, in that the guide path comprises an arc-shaped strip, preferably made of metal, which has an essentially smooth sliding plane for the resilient element. The cross-sectional shape of the sliding plane can, if necessary, be matched to the cross-sectional shape of the resilient element. The arc-shaped strip then forms a guide channel which has a sliding plane on the inside.

The resilient element can move along the guide channel with very little friction. Wire-like coupling means made of plastic, such as nylon, will make contact with the guide path because of the arc shape of the latter, so that there will be some question of friction. This friction is very small if the guide path has a smooth metal sliding plane.

In the case of a tubular guide, the internal dimensions of the tube will be matched to the cross-section of the resilient element.

The guide for the resilient element can comprise a tube, an arc-shaped strip or both. However, the guide can also be formed in another way, for example by means of a rail. The tube or the guide strip can be made of a wear-resistant plastic, such as teflon.

According to the invention, it is also advantageous if the spring constant (C) of the resilient element decreases on further extension of the resilient element, preferably from a certain spring force (F) or extension (L). The equation F=C×L gives the relationship between the spring force, the spring constant and the extension here. If the resilient element has to become a little longer when the patient moves his or her head, a resilient element of this type ensures that the additional forces exerted on the teeth remain relatively small. This is particularly advantageous when the head is not only turned to the left or right but is also tilted a little up or down, such as, for example, when nodding to indicate yes. In this context, it is particularly advantageous, according to the invention, if, above a certain spring force or extension of the resilient element, the spring force of said element remains essentially constant on further extension thereof. Resilient elements of this type are known per se and can be produced, for example, from wires made of a so-called Nitinol alloy. Nitinol is a so-called super-elastic nickel-titanium alloy. Nitinol wires of this type are known in orthodontics because of their particular elastic properties and are fitted in the mouth as aids when correcting the position of incisors or molars. Nitinol wires are described in, for example, U.S. Pat. No. 4,037,324 and are described more extensively in the literature references cited in column 7 of U.S. Pat. No. 4,037,324, which literature references are incorporated in the present Application by way of reference.

Nitinol wires are marketed by, amongst other companies, GAC International Inc., New York, USA and TP Orthodontics Inc., La Porte, Ind., USA, under the trade names Sentalloy® and Reflex® respectively.

The invention also relates to an orthodontic aid provided with a tensioning system according to the invention.

The invention will be explained in more detail below with the aid of an illustrative embodiment shown in the drawing. In the drawing.

Figure 1:
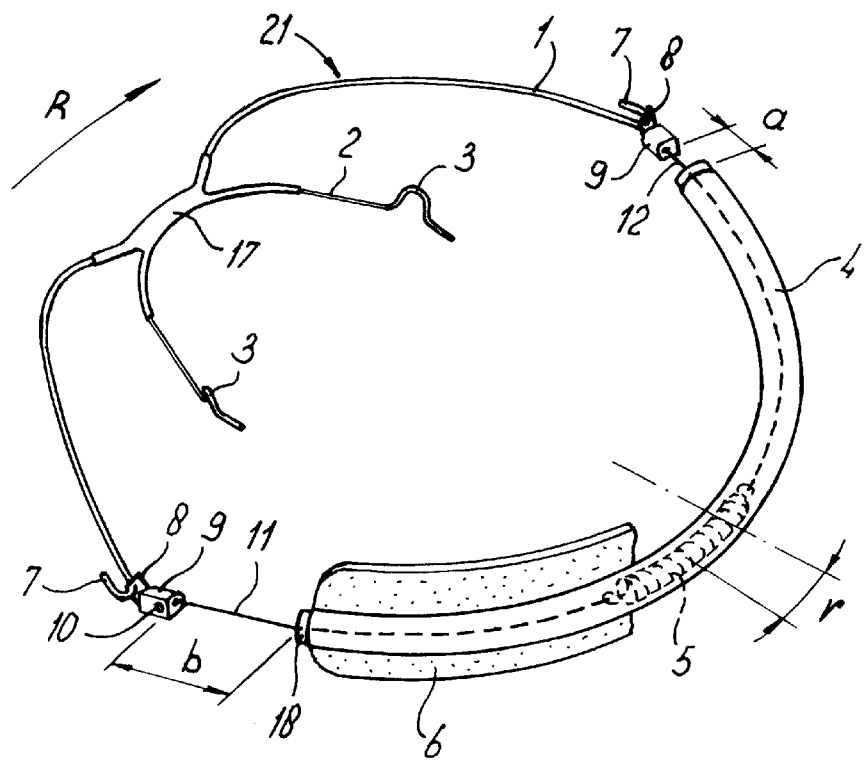
FIG. 1 shows a perspective view of a tensioning system according to the invention with an outer brace.

FIG. 1 shows a known outer brace, indicated by 21, with outer arms 1, to which the inner arms 2 are fixed at 17. Bends are formed in the inner arms 2 at 3, the free ends of said bends being used for fixing the inner arms to the teeth. The outer brace 21 is provided, at its ends which are located outside the patient's mouth during use, with U-shaped hooks 7.

The tensioning system according to the invention comprises a helical spring 5, which at its opposing ends is fixed to one end of cord 11, and, respectively, to one end of cord 12. The other ends of cords 11 and 12, respectively, are clamped by means of a screw 10 in a shoe 9. The shoes 9 are provided with safety hooks 8, which can be coupled to the hooks 7 of the outer brace 21.

Figure 5:
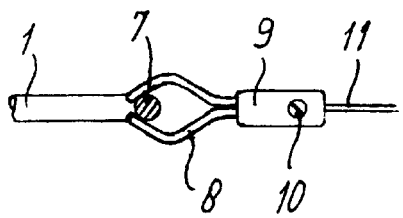
FIG. 5 shows a detail, partially in cross-section, of the fixing of the coupling means to the outer brace.

FIG. 5 shows, in detail, the fixing of a safety hook 8 to a U-shaped hook 7, which is shown partially, in cross-section. The legs of the safety hook are able to spread apart resiliently, so that the linkage is broken if a certain tensile force, for example of 1000 gram, is exerted.

The safety hooks 8 are thus uncoupled if a pull of a certain force is exerted on the outer brace 1.

Figure 2:
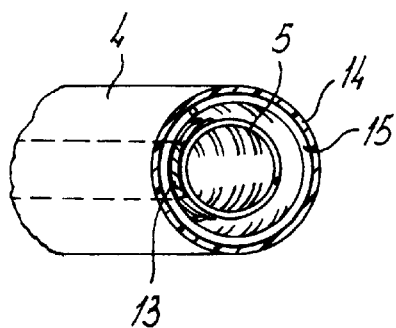
FIG. 2 shows a detail of a tensioning system according to the invention.

The spring 5 is fitted in a flexible tube 4, a detailed view of which is shown in FIG. 2.

Figure 3:
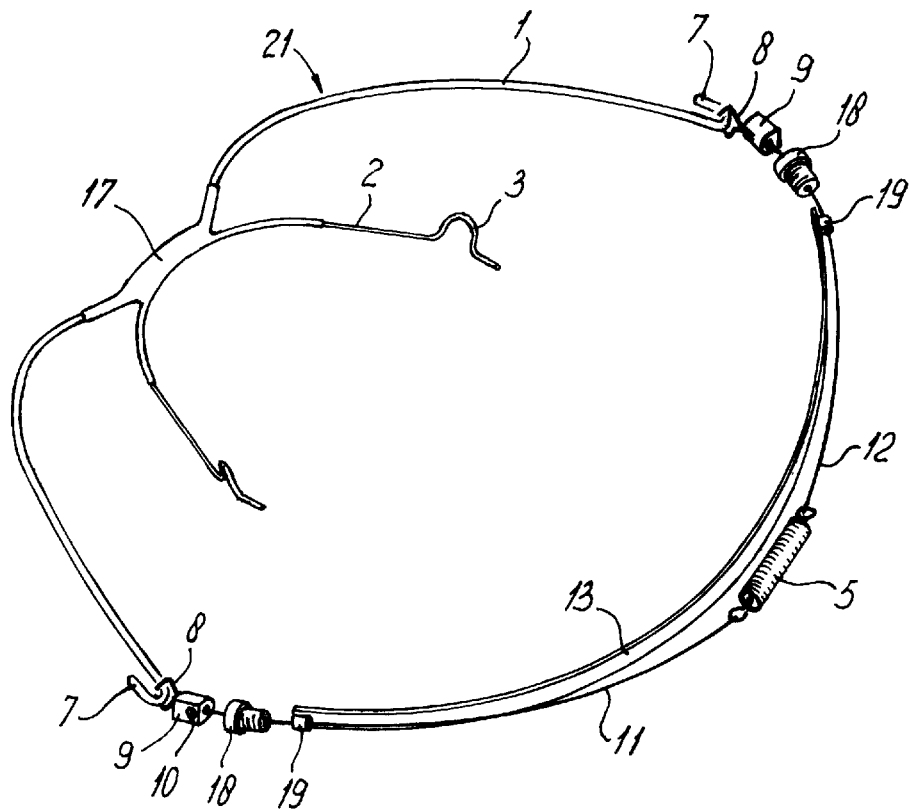
FIG. 3 shows a perspective view of a tensioning system according to the invention with an outer brace: in this figure the enclosing tube for the tensioning system has been omitted.

FIG. 3 shows the tensioning system according to the invention together with an orthodontic brace, the tube 4 being omitted in this figure. FIG. 3 clearly shows the arc-shaped guide 13 in the form of a metal strip which has an essentially smooth sliding plane. Stops 19, in the form of small tubes through which the wires 11 and 12 pass, are fixed at the ends of the guide path. Said stops 19 ensure that the spring can not run off the guide path. The guide path 13 having a smooth sliding plane matched to the shape of the spring makes it possible for the spring 5 to be able to be moved smoothly along the guide path without jolts or vibrations. FIG. 3 also shows bush-shaped plugs 18, which can be fitted in the ends of the tube 4. Said plugs are provided with longitudinal holes for the wires 10 and 11.

FIG. 2 shows a detailed view of a tube 4 according to the invention. Said tube 4 is formed from a helical spring 15 which is covered on the outside by a covering 14, for example a so-called shrink sleeve. Said covering 14 ensures that none of the patient's hair can get caught between the windings of the helical spring 15. The whole easily adjusts to the shape of the patient's neck.

Figure 4:
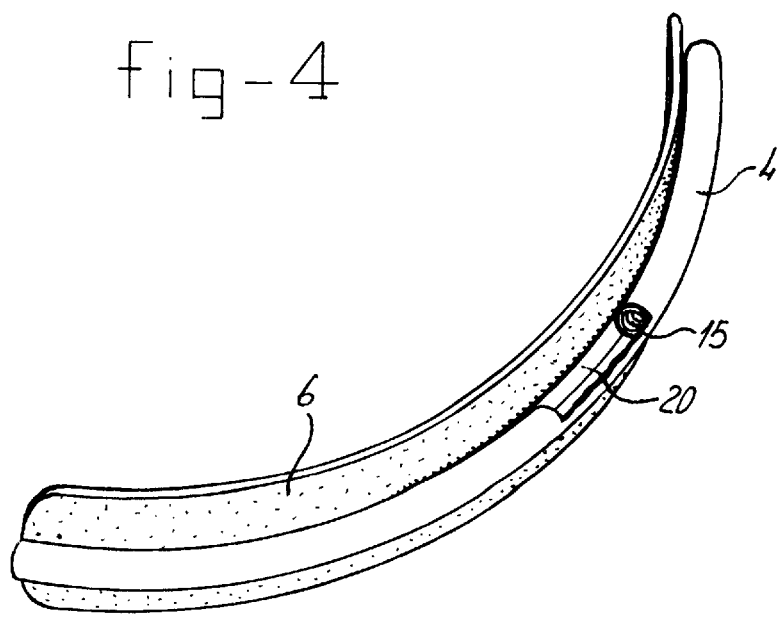
FIG. 4 shows a detail of a tensioning system according to the invention, showing the fixing of the tensioning system to a neck band.

The tensioning system according to the invention fitted in the tube 4 can, as can be seen from FIG. 4, be fixed by means of, for example, a Velcro fastening to a neck band 6, which is known per se. Said neck band 6 to some extent distributes the pressure over the neck and can easily be replaced when it has become soiled.

The way in which the tensioning system according to the invention which is shown in the drawing is fitted on the patient largely corresponds to the fitting method as described in U.S. Pat. No. 3,526,035. The inner arms are placed in the mouth, the tensioning system is placed on the neck and the hooks 8 and 7 are engaged on either side of the patient's head. The orthodontist can adjust the pre-tensioning of the spring 5 by means of the screws 10 which clamp the cords 11 and 12 in the shoes 9.

When fitting the tensioning system and the brace, the tube 4 adapts, because of its flexibility, to the shape of the patient's neck. Providing it is sufficiently flexible, the tube also continues to adjust during use to the shapes of the neck, which, for example, is very pleasant when the patient is sleeping.

In FIG. 1, arrows show, diagrammatically, the functioning of the tensioning system according to the invention. In this figure, the patient is imagined to have turned his or her head to the right in accordance with arrow R. As a result of this movement, the centre of the spring 5 has moved in accordance with arrow r. The distance r over which the centre of the spring 5 has moved is equal to the difference between the distances b and a, which show the respective distances between the shoes 9 and stops 18. The entire unit comprising the outer arms 1 of the outer brace 21, cord 11, spring 5 and cord 12, thus forms, as it were, a "ring" which partially passes through the tube 4, which "ring" turns as the patient's head is turned, whilst the tube 4, which is fixed relatively firmly to the patient's neck, remains in place unchanged. It will be clear that with this arrangement the tensioning force of the spring can remain constant because the spring 5 slides along the guide 13 through the tube 4. If the head is turned in a purely rotary movement, R is equal to r.

The friction between, on the one hand, the arc-shaped guide 13 and the resilient element 5 and, on the other hand, between the arc-shaped guide and the coupling element 11, such as a plastic cord, is very small with this arrangement, so that said friction has hardly any influence on the forces exerted on the teeth. This is highly advantageous from the standpoint of orthodontic considerations and for comfort in wear.

Figure 6:
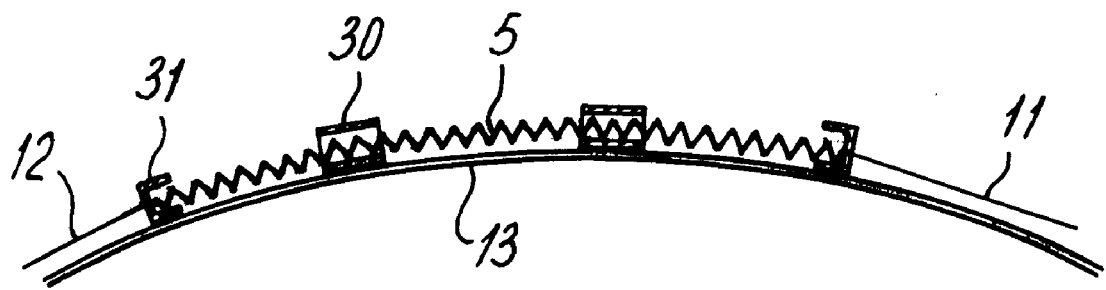
FIG. 6 shows, in diagrammatic longitudinal section, a detail of a particularly advantageous embodiment of the tensioning system according to the invention.

FIG. 6 shows, diagrammatically, an embodiment of the tensioning system in which a metal spring 5 is able to move with low friction, without shocks and virtually soundlessly, i.e. barely audibly, over a metal guide path 13. To this end, plastic sleeves 30 are fitted around the spring 5 and sleeves 31, which are closed at one end and to which the cords 11 and 12 are also fixed, are fixed to the ends of the spring. The sleeves 30, 31 prevent direct metal-on-metal contact and make it possible for the spring to move smoothly backwards and forwards along the guide path. Smoothing down the sleeves 30, and preferably also the sleeves 31, somewhat on the side where said sleeves make contact with the guide path 13 prevents a screw movement of the spring with respect to the sleeves 30 from being able to take place, so that said sleeves 30 do not start to move along the spring.

Figure 7A:
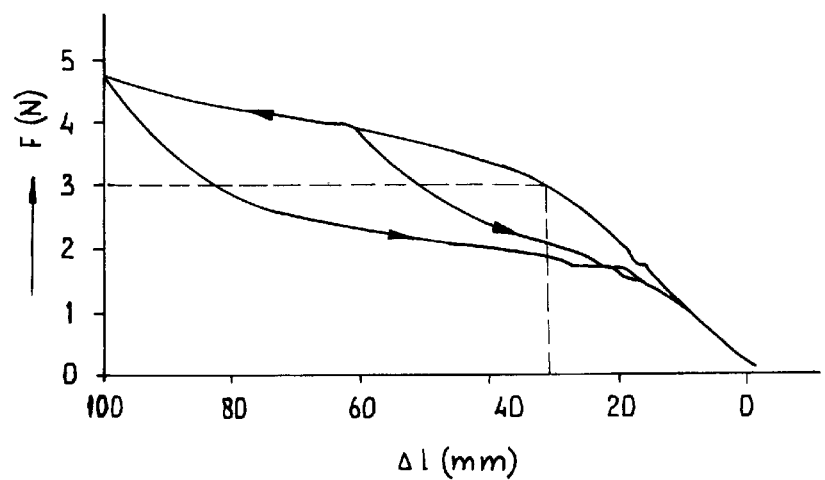
FIGS. 7a and 7b show graphs of spring characteristics of a helical spring according to the invention made from Nitinol wire.
Figure 7B:
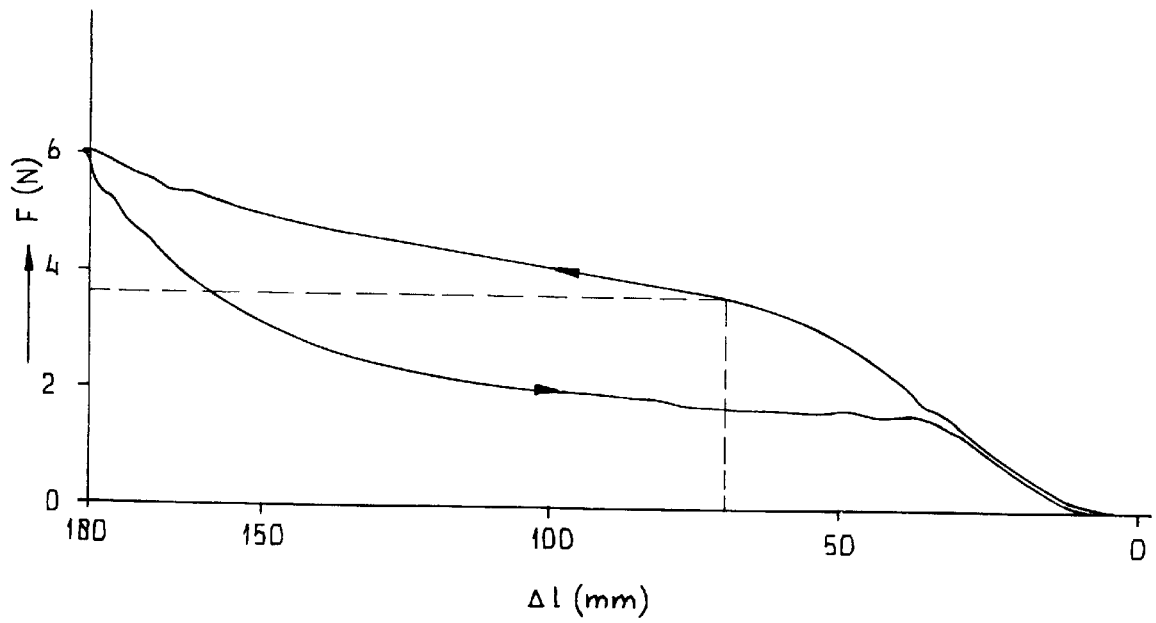

FIGS. 7a and 7b show spring characteristics of two different helical springs made of Nitinol wire. In these graphs the abscissa shows the elongation Δl in mm, whilst the ordinate shows the spring force F in N. Both springs had an internal diameter of 2.0 mm and an external diameter of 2.8 mm. The spring used for FIG. 7a had an unloaded length of 15 mm and the spring used for FIG. 7b had an unloaded length of 20 mm. The arrows shown on the curves in FIGS. 7a and 7b indicate the direction of movement of the spring. In these graphs an arrow pointing to the left indicates the spring characteristic during extension, whilst an arrow pointing to the right indicates the spring characteristic when the load on the spring is relaxed.

It can be seen that, for the spring in FIG. 7a above a spring force of about 3 N (about 300 g) and from an extension of about 30 mm, the spring constant decreases on further extension, which signifies that the gradient of the plot of the spring force against the extension becomes smaller. From an extension of 30 mm, which corresponds to a spring force of 3 N, this spring can be subjected to substantial additional extensions, for example up to 80 mm, whilst the spring force increases by only about 1 N.

Something similar applies in the case of the spring constant for the spring from FIG. 7b. However, the boundary in this case is at a spring force of about 3.8 N and an extension of about 70 mm.

Springs having this type of spring characteristic, as described above, can be used highly advantageously in a tensioning system according to the invention. After all, a specific spring force, which can be utilised for correction of the teeth, has to be achieved with a relatively small extension of the spring, relatively little of the freedom of movement over the guide path being lost. If, when certain movements are made, such as a nodding movement to indicate yes, the circumference of the, as it were, "closed ring", has to increase, springs of this type can be subjected to a relatively large extension with a relatively small increase in the spring force, as a result of which the additional forces exerted on the teeth remain limited. The patient's freedom of movement and the comfort in wear can be appreciably improved by this means.

When the patient's head makes more complex movements and nodding movements to indicate yes, the spring 5 will frequently also have to extend in order to make these movements possible. The forces exerted on the teeth will change as a result, which is adverse for the treatment and reduces comfort in wear. This can be counteracted or prevented by using, as the resilient element, an element for which the spring force increases only slightly or does not increase at all on further extension of the spring.

It is pointed out that the tensile forces which are to be exerted on the teeth and are customary and desired in orthodontics are generally less than 500 gram. These tensile forces are frequently 100–150 gram and sometimes 300–400 gram. It will be clear that with such relatively small forces the effect of friction can easily become apparent. Friction must therefore be very low.

If the element used as the resilient element is an element for which the spring force remains essentially constant after a specific spring force is reached, or for which the spring constant decreases on further extension after a specific spring force or extension is reached, it will be possible to take the abovementioned tensile forces customary in orthodontics as the so-called specific spring force. Said specific spring force will then in general be less than 500 gram. Depending on the correction of the teeth to be carried out and on the circumstances, this spring force will frequently be between 100 and 400 to 500 gram. In practice, tensile forces of 200 or 400 gram are found to be highly advantageous.

As can be seen from FIG. 1, the spring 5 can move freely to the right or to the left in the longitudinal direction of the tube 4. Because the coupling elements 11 and 12 extend continuously from the ends of the spring 5 to the shoes 9 fitted to the hooks 7 and 8 of the outer brace, a maximum freedom of movement for the patient's head is obtained. After all, the spring can, in principle, be moved unhindered along the entire guide path. The patient can, therefore, turn his or her head freely and unhindered in a movement of shaking the head to indicate no. With this arrangement, the tensile forces to be exerted on the teeth will remain essentially constant, until the spring 5 or a shoe 9 comes to rest against a stop 19 or, respectively, a stop 18. When, as will preferably be the case, the resilient element has a spring constant which decreases after a specific extension or spring force is reached, the increase in the tensile force which occurs on one side of the teeth after this contact is made will be restricted or relatively small. A spring of this type for which the spring constant decreases after a specific extension or tensile force is reached also increases the comfort in wear and the freedom of movement with regard to nodding movements of the head to indicate yes, during which such a spring will necessarily be extended.

It will be clear that many variants of the tensioning system according to the invention are conceivable, such as, for example:
   the resilient element can be, for example, an elastic band, etc.;
   the guide path can be formed by an arc-shaped strip, a tube, a rail, etc., the important factor here being mainly that the resilient element can be moved along without jerks;

cords, cables, strips, etc. can be used as the coupling means;

the flexibility of the tube 4 can also be achieved in some other way than by means of a spiral-shaped winding 15;

the spiral-shaped winding 15 can be made of metal, plastic and the like. The lighter the weight, the better;

the guide path 13 can also be made of a plastic, which is preferably wear-resistant and causes minimal friction;

a resilient element having the resilient special characteristics as explained in this Application, such as a helical spring made of Nitinol wire, can also be used as an immovable tensioning means. Some of the advantages of the invention will then be lost.

I claim:

1. A tensioning system for an extra-oral orthodontic outer brace comprising an extra-oral tensioning element for exerting a tensile force, wherein said element has a spring constant that decreases when said element is extended beyond a predetermined length and a neck brace in which said element is carried for being worn on a neck of a wearer.

2. An orthodontic device comprising an extra-oral outer brace and a tensioning system for exerting a tensile force on said outer brace, said tensioning system comprising a coil spring of super-elastic nickel-titanium alloy wire connected to said outer brace.

3. The device of claim 2, wherein said tensioning system further comprises a neck brace in which said coil spring is carried.

* * * * *